United States Patent
Kirihara et al.

(10) Patent No.: US 11,331,311 B2
(45) Date of Patent: May 17, 2022

(54) PROPHYLACTIC AND/OR THERAPEUTIC AGENT CONTAINING PYRIDYLAMINOACETIC ACID COMPOUND

(71) Applicant: SANTEN PHARMACEUTICAL CO., LTD., Osaka (JP)

(72) Inventors: Tomoko Kirihara, Ikoma (JP); Atsushi Shimazaki, Osaka (JP); Najam A. Sharif, Emeryville, CA (US)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/815,575

(22) Filed: Mar. 11, 2020

(65) Prior Publication Data

US 2020/0206200 A1 Jul. 2, 2020

Related U.S. Application Data

(63) Continuation of application No. 15/742,705, filed as application No. PCT/JP2016/070110 on Jul. 7, 2016, now abandoned.

(30) Foreign Application Priority Data

Jul. 9, 2015 (JP) .............................. JP2015-137968

(51) Int. Cl.
*A61K 31/444* (2006.01)
*A61P 27/06* (2006.01)
*A61P 27/02* (2006.01)
*A61K 9/00* (2006.01)

(52) U.S. Cl.
CPC .......... *A61K 31/444* (2013.01); *A61K 9/0048* (2013.01); *A61P 27/02* (2018.01); *A61P 27/06* (2018.01)

(58) Field of Classification Search
None
See application file for complete search history.

(56) References Cited

U.S. PATENT DOCUMENTS

| | | | |
|---|---|---|---|
| 8,648,097 B2 | 2/2014 | Iwamura et al. | |
| 8,685,986 B2 * | 4/2014 | Hagihara | A61K 31/506 514/256 |
| 9,339,496 B2 * | 5/2016 | Kirihara | A61K 31/5575 |
| 9,415,038 B2 | 8/2016 | Shams et al. | |
| 2011/0054172 A1 | 3/2011 | Iwamura et al. | |
| 2012/0190852 A1 | 7/2012 | Hagihara et al. | |
| 2014/0018350 A1 | 1/2014 | Kirihara et al. | |
| 2014/0018396 A1 | 1/2014 | Kirihara et al. | |
| 2014/0148416 A1 | 5/2014 | Kakizuka et al. | |
| 2015/0196541 A1 | 7/2015 | Shams et al. | |
| 2016/0317512 A1 | 11/2016 | Endo | |
| 2016/0317664 A1 | 11/2016 | Endo | |
| 2016/0324838 A1 | 11/2016 | Shams et al. | |
| 2018/0169079 A1 | 6/2018 | Shams et al. | |

FOREIGN PATENT DOCUMENTS

| | | |
|---|---|---|
| CN | 102448940 A | 5/2012 |
| EP | 3093018 A1 | 11/2016 |
| JP | 2002-179694 A | 6/2002 |
| JP | 2014-019650 A | 2/2014 |
| JP | 2014-031369 A | 2/2014 |
| WO | 2010/113957 A1 | 10/2010 |
| WO | 2012/043891 A1 | 4/2012 |

OTHER PUBLICATIONS

International Search Report (PCT/ISA/210) dated Aug. 2, 2016, by the Japanese Patent Office as the International Searching Authority for International Application No. PCT/JP2016/070110.
Written Opinion (PCT/ISA/237) dated Aug. 2, 2016, by the Japanese Patent Office as the International Searching Authority for International Application No. PCT/JP2016/070110.
Ihekoromadu et al.: "Safety and Efficacy of DE-117, a Selective EP2 Agonist in a Phase 2a Study," Investigative Ophthalmology & Visual Science, vol. 56, No. Issue, Jun. 2015, p. 5708.
Extended Search Report issued by the European Patent Office in corresponding European Patent Application No. 16821453.4-1112 dated Jul. 2, 2018 (6 pages).
The First Official Action issued by the Taiwan Intellectual Property Office in corresponding Taiwanese Patent Application No. 105121523 dated Nov. 4, 2019 (4 pages).
Decision of Refusal dated Oct. 12, 2020, by the Japanese Patent Office in corresponding Japanese Patent Application No. 2017-527490 and an English translation of the Decision. (5 pages).
Communication pursuant to Article 94(3) EPC dated Dec. 17, 2020, by the European Patent Office in corresponding European Patent Application No. 16 821 453.4 (5 pages).
Jonas et al., "Ocular Hypertension: General Characteristics and Estimates Cerebrospinal Fluid Pressure. The Beijing Eye Study 2011", PLOS ONE, Jul. 2014, vol. 9, No. 7, pp. e100533, XP055759317. (8 pages).
"Remarks from medical specialists in Kansai || Doctor's column", [online] Sep. 23, 2010, [searched on Oct. 18, 2021], <URL:https://web.archive.org/web/20100923074818/https://eonet.jp/health/doctor/column19_1.html>, and an English translation (12 pages).
Notice of Reasons for Refusal dated Oct. 27, 2021, by the Japanese Patent Office in corresponding Japanese Patent Application No. 2017-527490, and an English translation of the Notice. (48 pages).

* cited by examiner

*Primary Examiner* — Heidi Reese
(74) *Attorney, Agent, or Firm* — Buchanan, Ingersoll & Rooney PC

(57) ABSTRACT

The object of the present invention is to find a new application of isopropyl (6-{[4-(pyrazol-1-yl)benzyl](pyridin-3-ylsulfonyl)aminomethyl}pyridin-2-ylamino)acetate or a salt thereof. Isopropyl (6-{[4-(pyrazol-1-yl)benzyl](pyridin-3-ylsulfonyl) aminomethyl}pyridin-2-ylamino) acetate or a salt thereof is useful as a therapeutic agent for a disease involving a greatly elevated intraocular pressure.

5 Claims, No Drawings

PROPHYLACTIC AND/OR THERAPEUTIC AGENT CONTAINING PYRIDYLAMINOACETIC ACID COMPOUND

CROSS-REFERENCE OF RELATED APPLICATIONS

This application is a continuation application of U.S. patent application Ser. No. 15/742,705 filed on Jan. 8, 2018, now abandoned, which in turn is a 371 of International Application PCT/JP2016/070110 filed on Jul. 7, 2016, which claims priority from Japanese Application No. 2015-137968 filed on Jul. 9, 2015, the disclosures of all of which are incorporated in their entirety by reference herein.

TECHNICAL FIELD

The present invention relates to a prophylactic and/or therapeutic agent containing isopropyl (6-{[4-(pyrazol-1-yl)benzyl](pyridin-3-ylsulfonyl)aminometh yl}pyridin-2-ylamino)acetate or a salt thereof.

BACKGROUND ART

Glaucoma is an eye disease in which an elevated intraocular pressure due to various causes may damage the tissues (retina, optic nerve, and the like) inside the eyeball and lead to visual loss. In general, intraocular pressure-lowering therapies have been employed as treatment methods for glaucoma, and representative intraocular pressure-lowering therapies include drug therapies, laser therapies, surgical therapies, and the like.

Here, for treating some types of glaucoma, for example, primary angle closure glaucoma, a treatment of rapidly lowering the greatly elevated intraocular pressure has been conducted by intravenous administration, oral administration, or the like of acetazolamide before radical treatment such as iridotomy. However, it cannot be said that this treatment is sufficient in terms of safety and efficacy, and there has been a demand for a new drug therapy which is safer, and which lowers the greatly elevated intraocular pressure more rapidly.

Isopropyl (6-{[4-(pyrazol-1-yl)benzyl](pyridin-3-ylsulfonyl)aminometh yl}pyridin-2-ylamino) acetate is a compound represented by the following formula (1) and described in Patent Literature 1 as one of the numerous pyridylaminoacetic acid compounds:

[Chem. 1]

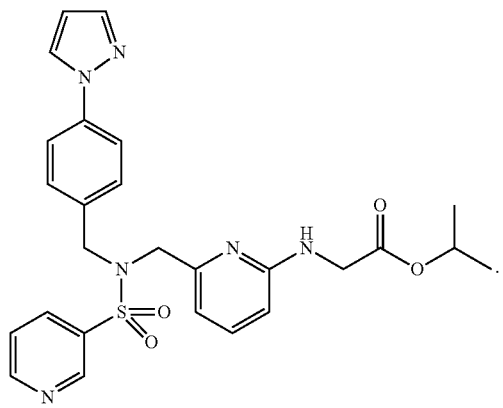

(1)

In addition, it is stated that these pyridylaminoacetic acid compounds have EP2 agonist action (Patent Literature 2), and are expected to have intraocular pressure-lowering activity, and may be used as a therapeutic agent for glaucoma (Patent Literature 1).

Moreover, Patent Literatures 3 and 4 state that a combination of the compound represented by the above-described formula (1) with another therapeutic agent for glaucoma such as timolol increases the intraocular pressure-lowering activity. Note that the entire contents described in Patent Literatures 1 to 4 are incorporated herein by reference.

However, there has been no report on the point that the compound represented by the above-described formula (1) or a salt thereof can lower a greatly elevated intraocular pressure rapidly and safely.

CITATION LIST

Patent Literature

[Patent Literature 1] United States Patent Application Publication No. 2012/0190852
[Patent Literature 2] United States Patent Application Publication No. 2011/0054172
[Patent Literature 3] United States Patent Application Publication No. 2014/0018396
[Patent Literature 4] United States Patent Application Publication No. 2014/0018350

SUMMARY OF INVENTION

An object of the present invention is to find a new medicinal use of the above-described compound represented by the formula (1) or a salt thereof.

To achieve the above-described object, the present inventors have conducted intensive studies, and found that isopropyl (6-{[4-(pyrazol-1-yl)benzyl](pyridin-3-ylsulfonyl) aminometh yl}pyridin-2-ylamino)acetate or a salt thereof (hereinafter, also referred to as "the present compound") lowers a greatly elevated intraocular pressure safely and rapidly. This finding has led to the completion of the present invention.

Specifically, the present invention relates to the following.
[1] A prophylactic and/or therapeutic agent for a disease involving a greatly elevated intraocular pressure, comprising isopropyl (6-{[4-(pyrazol-1-yl)benzyl](pyridin-3-ylsulfonyl)aminometh yl}pyridin-2-ylamino)acetate or a salt thereof.
[2] The prophylactic and/or therapeutic agent according to the above-described item [1], wherein
the disease involving a greatly elevated intraocular pressure is acute primary angle closure, primary angle closure glaucoma, secondary angle closure glaucoma, or acute intraocular pressure elevation.
[3] The prophylactic and/or therapeutic agent according to the above-described item [1] or [2], comprising 0.001 to 0.03% (w/v) of the isopropyl (6-{[4-(pyrazol-1-yl)benzyl](pyridin-3-ylsulfonyl)aminometh yl}pyridin-2-ylamino)acetate or the salt thereof.
[4] The prophylactic and/or therapeutic agent according to any one of the above-described items [1] to [3], which does not comprise any other prophylactic and/or therapeutic agent for glaucoma or ocular hypertension than isopropyl (6-{[4-(pyrazol-1-yl)benzyl](pyridin-3-ylsulfonyl)aminometh yl}pyridin-2-ylamino)acetate or a salt thereof.

[5] An eye drop, comprising the prophylactic and/or therapeutic agent according to any one of the above-described items [1] to [4].
[6] Isopropyl (6-{[4-(pyrazol-1-yl)benzyl](pyridin-3-ylsulfonyl)aminometh yl}pyridin-2-ylamino)acetate or a salt thereof for the use of preventing and/or treating a disease involving a greatly elevated intraocular pressure.
[7] Isopropyl (6-{[4-(pyrazol-1-yl)benzyl](pyridin-3-ylsulfonyl)aminometh yl}pyridin-2-ylamino)acetate or a salt thereof according to the above-described item [6], wherein the disease involving a greatly elevated intraocular pressure is acute primary angle closure, primary angle closure glaucoma, secondary angle closure glaucoma, or acute intraocular pressure elevation.
[8] An eye drop, comprising isopropyl (6-{[4-(pyrazol-1-yl)benzyl](pyridin-3-ylsulfonyl)aminometh yl}pyridin-2-ylamino)acetate or a salt thereof according to the above-described item [6] or [7].
[9] Use of isopropyl (6-{[4-(pyrazol-1-yl)benzyl](pyridin-3-ylsulfonyl)aminometh yl}pyridin-2-ylamino)acetate or a salt thereof for preparing a prophylactic and/or therapeutic agent for a disease involving a greatly elevated intraocular pressure.
[10] The use according to the above-described item [9], wherein the disease involving a greatly elevated intraocular pressure is acute primary angle closure, primary angle closure glaucoma, secondary angle closure glaucoma, or acute intraocular pressure elevation.
[11] The use according to the above-described item [9] or [10], comprising 0.001 to 0.03% (w/v) of the isopropyl (6-{[4-(pyrazol-1-yl)benzyl](pyridin-3-ylsulfonyl)aminometh yl}pyridin-2-ylamino)acetate or the salt thereof.
[12] The use according to any one of the above-described items [9] to [11], which does not use any other prophylactic and/or therapeutic agent for glaucoma or ocular hypertension than isopropyl (6-{[4-(pyrazol-1-yl) benzyl](pyridin-3-ylsulfonyl) aminometh yl}pyridin-2-ylamino)acetate or a salt thereof.
[13] The use according to any one of the above-described items [9] to [12], wherein the prophylactic and/or therapeutic agent is an eye drop.
[14] A method for preventing and/or treating a disease involving a greatly elevated intraocular pressure, comprising administering isopropyl (6-{[4-(pyrazol-1-yl) benzyl](pyridin-3-ylsulfonyl) aminometh yl}pyridin-2-ylamino) acetate or a salt thereof to patients with said disease which has to be prevented and/or treated.
[15] The method according to the above-described item [14], wherein the disease involving a greatly elevated intraocular pressure is acute primary angle closure, primary angle closure glaucoma, secondary angle closure glaucoma, or acute intraocular pressure elevation.
[16] The method according to the above-described item [14] or [15], wherein the administration amount of the isopropyl (6-{[4-(pyrazol-1-yl) benzyl](pyridin-3-ylsulfonyl) aminometh yl}pyridin-2-ylamino)acetate or the salt thereof is 0.001 to 0.03% (w/v).
[17] The method according to any one of the above-described items [14] to [16], wherein any other prophylactic and/or therapeutic agent for glaucoma or ocular hypertension than isopropyl (6-{[4-(pyrazol-1-yl) benzyl](pyridin-3-ylsulfonyl) aminometh yl}pyridin-2-ylamino)acetate or a salt thereof is not administered.
[18] The method according to any one of the above-described items [14] to [17], wherein the administration is instillation.

Note that it is possible to combine any two or more selected from the above-described configurations [1] to [5]. It is possible to combine any two or more selected from the above-described configurations [6] to [8], and the explanations regarding "prophylactic and/or therapeutic agent" in this specification may also be applied to these embodiments regarding said "isopropyl (6-{[4-(pyrazol-1-yl)benzyl](pyridin-3-ylsulfonyl)aminometh yl}pyridin-2-ylamino)acetate or a salt thereof." It is also possible to combine any two or more selected from the above-described configurations [9] to [13], and the explanations regarding "prophylactic and/or therapeutic agent" in this specification may also be applied to these embodiments regarding said "use." It is also possible to combine any two or more selected from the above-described configurations [14] to [18], and the explanations regarding "prophylactic and/or therapeutic agent" in this specification may also be applied to these embodiments regarding said "method."

DESCRIPTION OF EMBODIMENTS

Hereinafter, embodiments of the present invention are described in detail. Note that, in the following description, the "prophylactic and/or therapeutic agent" of the present invention is simply referred to as "therapeutic agent", unless otherwise noted.

Isopropyl (6-{[4-(pyrazol-1-yl)benzyl](pyridin-3-ylsulfonyl)aminometh yl}pyridin-2-ylamino) acetate or a salt thereof contained in the therapeutic agent of the present invention can be produced according to the method described in United States Patent Application Publication No. 2012/0190852 (Patent Literature 1), an ordinary method in the technical field, or the like.

The salt of isopropyl (6-{[4-(pyrazol-1-yl)benzyl](pyridin-3-ylsulfonyl)aminometh yl}pyridin-2-ylamino)acetate contained in the therapeutic agent of the present invention is not particularly limited, as long as the salt is pharmacologically acceptable. Specifically, the salt may be an inorganic acid salt such as hydrochloric acid salt, hydrobromic acid salt, hydroiodic acid salt, nitric acid salt, sulfuric acid salt, or phosphoric acid salt; an organic acid salt such as acetic acid salt, trifluoroacetic acid salt, benzoic acid salt, oxalic acid salt, malonic acid salt, succinic acid salt, maleic acid salt, fumaric acid salt, tartaric acid salt, citric acid salt, methanesulfonic acid salt, ethanesulfonic acid salt, trifluoromethanesulfonic acid salt, benzenesulfonic acid salt, p-toluenesulfonic acid salt, glutamic acid salt, or aspartic acid salt; or the like. The salt is preferably a hydrochloric acid salt or a trifluoroacetic acid salt.

The content of isopropyl (6-{[4-(pyrazol-1-yl)benzyl](pyridin-3-ylsulfonyl)aminometh yl}pyridin-2-ylamino)acetate or the salt thereof in the therapeutic agent of the present invention is not particularly limited. In the case of an eye drop, the lower limit of the content is preferably 0.0003% (w/v), more preferably 0.001 (w/v), further preferably 0.0013% (w/v), and particularly preferably 0.0015% (w/v). Meanwhile, the upper limit of the content is preferably 0.03% (w/v), more preferably 0.01% (w/v), further preferably 0.005% (w/v), particularly preferably 0.003% (w/v), and especially preferably 0.0027% (w/v). More specifically, the content is preferably 0.0003 to 0.03% (w/v), more preferably 0.001 to 0.01% (w/v), further preferably 0.001 to 0.005% (w/v), particularly preferably 0.001 to 0.003% (w/v), especially preferably 0.0013 to 0.003% (w/v), and still further preferably 0.0015 to 0.0027% (w/v). More specifically, the content is preferably 0.0010% (w/v), 0.0011% (w/v), 0.0012% (w/v), 0.0013% (w/v), 0.0014%

(w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v), 0.0029% (w/v), 0.0030% (w/v), 0.005% (w/v), 0.01% (w/v), or 0.03% (w/v), or the content is preferably in a range having an upper limit or a lower limit selected from any of these amounts. Here, the term "% (w/v)" means the mass (g) of an active ingredient (the present compound here) or an additive (surfactant or the like) contained per 100 mL of the eye drop. For example, 0.01% (w/v) of the present compound means that the content of the present compound per 100 mL of the eye drop is 0.01 g.

Note that, when a salt of isopropyl (6-{[4-(pyrazol-1-yl)benzyl](pyridin-3-ylsulfonyl)aminometh yl}pyridin-2-ylamino)acetate is contained, this content means that the content of isopropyl (6-{[4-(pyrazol-1-yl)benzyl](pyridin-3-ylsulfonyl)aminometh yl}pyridin-2-ylamino)acetate, which is the free form of the salt, is within the above-described range.

If necessary, additives can be used in the therapeutic agent of the present invention. As the additives, for example, a surfactant, a buffering agent, a tonicity adjusting agent, a stabilizer, an antiseptic agent, an antioxidant, a high-molecular weight polymer, and the like can be added.

In the therapeutic agent of the present invention, a surfactant usable as an additive for pharmaceuticals can be blended, as appropriate.

Examples of the surfactant include polyoxyethylene castor oils, polyoxyethylene hardened castor oils, polyoxyethylene sorbitan fatty acid esters, vitamin E TPGS, polyoxyethylene fatty acid esters, polyoxyethylene polyoxypropylene glycols, sucrose fatty acid esters, and the like.

More specifically, as the polyoxyethylene castor oils, various polyoxyethylene castor oils having different degrees of polymerization of ethylene oxide can be used. The degree of polymerization of ethylene oxide is preferably 5 to 100, more preferably 20 to 50, particularly preferably 30 to 40, and most preferably 35. Specific examples of the polyoxyethylene castor oils include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is the most preferable.

As the polyoxyethylene hardened castor oils, various polyoxyethylene hardened castor oils having different degrees of polymerization of ethylene oxide can be used. The degree of polymerization of ethylene oxide is preferably 10 to 100, more preferably 20 to 80, particularly preferably 40 to 70, and most preferably 60. Specific examples of the polyoxyethylene hardened castor oils include polyoxyethylene hardened castor oil 10, polyoxyethylene hardened castor oil 40, polyoxyethylene hardened castor oil 50, polyoxyethylene hardened castor oil 60, and the like, and polyoxyethylene hardened castor oil 60 is the most preferable.

The polyoxyethylene sorbitan fatty acid esters include polysorbate 80, polysorbate 60, polysorbate 40, polyoxyethylene sorbitan monolaurate, polyoxyethylene sorbitan trioleate, polysorbate 65, and the like, and polysorbate 80 is the most preferable.

Vitamin E TPGS is also referred to as tocopherol polyethylene glycol 1000 succinate.

The polyoxyethylene fatty acid esters include polyoxyl 40 stearate, and the like.

The polyoxyethylene polyoxypropylene glycols include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

The sucrose fatty acid esters include sucrose stearate and the like.

When a surfactant is blended in the therapeutic agent of the present invention, the content of the surfactant can be adjusted, as appropriate, according to the type of the surfactant and the like. Specifically, the lower limit is preferably 0.001% (w/v), more preferably 0.01% (w/v), further preferably 0.1% (w/v), particularly preferably 0.5% (w/v), and most preferably 0.8% (w/v). The upper limit is preferably 10% (w/v), more preferably 5% (w/v), further preferably 4% (w/v), particularly preferably 3% (w/v)), and most preferably 2% (w/v).

More specifically, the content is preferably 0.001 to 10% (w/v), more preferably 0.01 to 5% (w/v), further preferably 0.1 to 4% (w/v), particularly preferably 0.5 to 3% (w/v), and most preferably 0.8 to 2% (w/v).

In the therapeutic agent of the present invention, a buffering agent usable as an additive for pharmaceuticals can be blended, as appropriate.

Examples of the buffering agent include phosphoric acid, salts thereof, boric acid, salts thereof, citric acid, salts thereof, acetic acid, salts thereof, carbonic acid, salts thereof, tartaric acid, salts thereof, ε-aminocaproic acid, trometamol, and the like. More specifically, the salts of phosphoric acid include sodium phosphate, sodium dihydrogen phosphate, disodium hydrogen phosphate, potassium phosphate, potassium dihydrogen phosphate, dipotassium hydrogen phosphate, and the like; the salts of boric acid include borax, sodium borate, potassium borate, and the like; the salts of citric acid include sodium citrate, disodium citrate, trisodium citrate, and the like; the salts of acetic acid include sodium acetate, potassium acetate, and the like; the salts of carbonic acid include sodium carbonate, sodium hydrogen carbonate, and the like; the salts of tartaric acid include sodium tartrate, potassium tartrate, and the like. Especially, boric acid, salts thereof, citric acid, and salts thereof are preferable.

When a buffering agent is blended in the therapeutic agent of the present invention, the content of the buffering agent can be adjusted, as appropriate, according to the type of the buffering agent and the like, and is preferably 0.001 to 10% (w/v), more preferably 0.01 to 5% (w/v), further preferably 0.1 to 3% (w/v), and most preferably 0.2 to 2% (w/v).

In the therapeutic agent of the present invention, a tonicity adjusting agent usable as an additive for pharmaceuticals can be blended, as appropriate.

Examples of the tonicity adjusting agent include ionic tonicity adjusting agents, nonionic tonicity adjusting agents, and the like.

The ionic tonicity adjusting agents include sodium chloride, potassium chloride, calcium chloride, magnesium chloride, and the like. The nonionic tonicity adjusting agents include glycerin, propylene glycol, sorbitol, mannitol, and the like. When a tonicity adjusting agent is blended in the therapeutic agent of the present invention, the content of tonicity adjusting agent can be adjusted, as appropriate, according to the type of the tonicity adjusting agent and the like, and is preferably 0.01 to 10% (w/v), more preferably 0.02 to 7% (w/v), further preferably 0.1 to 5% (w/v), particularly preferably 0.5 to 4% (w/v), and most preferably 0.8 to 3% (w/v).

In the therapeutic agent of the present invention, a stabilizer usable as an additive for pharmaceuticals can be blended, as appropriate.

Examples of the stabilizer include edetic acid, monosodium edetate, disodium edetate, tetrasodium edetate, sodium citrate, and the like, and disodium edetate is particularly preferable. The sodium edetates may be hydrates. When a stabilizer is blended in the therapeutic agent of the present invention, the content of the stabilizer can be adjusted, as appropriate, according to the type of the stabilizer and the like, and is preferably 0.001 to 1% (w/v), more preferably 0.005 to 0.5% (w/v), and most preferably 0.01 to 0.1% (w/v).

In the therapeutic agent of the present invention, an antiseptic agent usable as an additive for pharmaceuticals can be blended, as appropriate.

Examples of the antiseptic agents include benzalkonium chloride, benzalkonium bromide, benzethonium chloride, sorbic acid, potassium sorbate, methyl paraoxybenzoate, propyl paraoxybenzoate, chlorobutanol, and the like. When an antiseptic agent is blended in the therapeutic agent of the present invention, the content of the antiseptic agent can be adjusted, as appropriate, according to the type of the antiseptic agent and the like, and is preferably 0.0001 to 1% (w/v), more preferably 0.0005 to 0.1% (w/v), further preferably 0.001 to 0.05% (w/v), and most preferably 0.005 to 0.010% (w/v).

In the therapeutic agent of the present invention, an antioxidant usable as an additive for pharmaceuticals can be blended, as appropriate.

Examples of the antioxidant include ascorbic acid, tocopherols, dibutylhydroxytoluene, butylhydroxyanisole, sodium erythorbate, propyl gallate, sodium sulfite, and the like. When an antioxidant is blended in the therapeutic agent of the present invention, the content of the antioxidant can be adjusted, as appropriate, according to the type of the antioxidant and the like, and is preferably 0.0001 to 1% (w/v), more preferably 0.0005 to 0.1% (w/v), and most preferably 0.001 to 0.05% (w/v).

In the therapeutic agent of the present invention, a high-molecular weight polymer usable as an additive for pharmaceuticals can be blended, as appropriate.

Examples of the high-molecular weight polymer include methyl cellulose, ethyl cellulose, hydroxymethyl cellulose, hydroxyethyl cellulose, hydroxypropyl cellulose, hydroxyethyl methyl cellulose, hydroxypropyl methyl cellulose, carboxymethyl cellulose, carboxy methyl cellulose sodium salt, hydroxypropyl methyl cellulose acetate succinate, hydroxypropyl methyl cellulose phthalate, carboxymethyl ethyl cellulose, cellulose acetate phthalate, polyvinylpyrrolidone, polyvinyl alcohol, carboxyvinyl polymer, polyethylene glycol, and the like.

When a high-molecular weight polymer is blended in the therapeutic agent of the present invention, the content of the high-molecular weight polymer can be adjusted, as appropriate, according to the type of the high-molecular weight polymer and the like, and is preferably 0.001 to 5% (w/v), more preferably 0.01 to 1% (w/v), and most preferably 0.1 to 0.5% (w/v).

The pH of the therapeutic agent of the present invention is preferably 4.0 to 8.0, more preferably 4.5 to 7.5, particularly preferably 5.0 to 7.0, and most preferably 5.5 to 6.5. To the therapeutic agent of the present invention, a pH adjusting agent for adjusting the pH may be added such as hydrochloric acid, phosphoric acid, citric acid, acetic acid, sodium hydroxide, potassium hydroxide, or the like.

The therapeutic agent of the present invention can be stored in containers produced from various materials. For example, a container made of polyethylene, polypropylene, or the like can be used. The therapeutic agent of the present invention is preferably stored in a polyethylene container from the viewpoints of the ease of instillation (hardness of the container), the stability of the present compound, and the like.

The dosage form of the therapeutic agent of the present invention is not particularly limited, as long as the dosage form is usable for pharmaceuticals. Specifically, the dosage form may be an eye drop, an ophthalmic injection, an ophthalmic ointment, or the like, and is particularly preferably an eye drop. These dosage forms of these drugs can be produced according to ordinary methods in the technical field. In addition, a solvent or dispersion medium used when the therapeutic agent of the present invention is a liquid agent is preferably water.

The therapeutic agent of the present invention may contain or may be used in combination with one or more, preferably 1 to 3, and more preferably 1 or 2 prophylactic and/or therapeutic agents for glaucoma or ocular hypertension other than the present compound. The other prophylactic and/or therapeutic agents for glaucoma or ocular hypertension are not particularly limited. Specifically, the other prophylactic and/or therapeutic agents are preferably therapeutic agents for glaucoma and the like which are commercially available or under development, more preferably commercially available therapeutic agents for glaucoma and the like, and particularly preferably commercially available therapeutic agents for glaucoma and the like which have different mechanisms of action from that of the present compound. More specifically, the other prophylactic and/or therapeutic agents include nonselective sympathomimetics, $\alpha_2$ receptor agonists, $\alpha_1$ receptor blockers, $\beta$ receptor blockers, parasympathomimetics, carbonic anhydrase inhibitors, prostaglandins, Rho kinase inhibitors, and the like.

A specific example of the nonselective sympathomimetics is dipivefrine. Specific examples of the $\alpha_2$ receptor agonists include brimonidine and apraclonidine. A specific example of the $\alpha_1$ receptor blocker is bunazosin. Specific examples of the $\beta$ receptor blockers include timolol, befunolol, carteolol, nipradilol, betaxolol, levobunolol, and metipranolol. A specific example of the parasympathomimetics is pilocarpine. Specific examples of the carbonic anhydrase inhibitors include dorzolamide, brinzolamide, and acetazolamide. Specific examples of the prostaglandins include latanoprost, isopropyl unoprostone, bimatoprost, and travoprost. A specific example of the Rho kinase inhibitors is ripasudil.

In an embodiment, the therapeutic agent of the present invention does not contain any other prophylactic and/or therapeutic agent for glaucoma or ocular hypertension than isopropyl (6-{[4-(pyrazol-1-yl) benzyl](pyridin-3-ylsulfonyl) aminometh yl}pyridin-2-ylamino)acetate or a salt thereof.

In an embodiment, the therapeutic agent of the present invention is not used in combination with any other prophylactic and/or therapeutic agent for glaucoma or ocular hypertension than isopropyl (6-{[4-(pyrazol-1-yl) benzyl](pyridin-3-ylsulfonyl) aminometh yl}pyridin-2-ylamino)acetate or a salt thereof.

The therapeutic agent of the present invention can be administered orally or parenterally. No special technique is required to prepare pharmaceutical preparations of the therapeutic agent, and the pharmaceutical preparations can be prepared by using commonly used techniques. The dosage forms for the administration include eye drops, ophthalmic ointments, injections, tablets, capsules, granules, powders, and the like, and eye drops are preferable.

The usage of the therapeutic agent of the present invention is not particularly limited, as long as the usage is enough to achieve a desired medicinal effect. A suitable usage can be selected, as appropriate, according to symptoms of the disease, the age and body weight of the patient, the dosage form of the agent, and the like. Specifically, 1 to 5 drops, preferably 1 to 3 drops, more preferably 1 to 2 drops, and particularly preferably 1 drop of the therapeutic agent of the present invention can be instilled 1 to 4 times a day, preferably 1 to 3 times a day, more preferably 1 to 2 times a day, and particularly preferably once a day, every day to every week. It is preferable to instill one drop of the therapeutic agent of the present invention once a day, every day. Here, 1 drop is generally approximately 0.01 to approximately 0.1 mL, preferably approximately 0.015 to approximately 0.07 mL, more preferably approximately 0.02 to approximately 0.05 mL, and particularly preferably approximately 0.03 mL.

The therapeutic agent of the present invention is a prophylactic and/or therapeutic agent for a disease involving a greatly elevated intraocular pressure, and is a pharmaceutical preparation used to rapidly reduce or lower the intraocular pressure.

In the present invention, the "disease involving a greatly elevated intraocular pressure" refers to a disease with an intraocular pressure in a range of, for example, from 25 to 100 mmHg, preferably from 25 to 80 mmHg, more preferably from 30 to 80 mmHg, and further preferably from 40 to 80 mmHg. For such a disease, it is necessary to rapidly lower the intraocular pressure.

The "greatly elevated intraocular pressure" which has to be treated or prevented by the present invention includes not only the so-called acute ocular hypertension state as in the case where the intraocular pressure is rapidly elevated to the above-described high intraocular pressure range in several weeks, several days, or several hours, but also the so-called chronic ocular hypertension state where the above-described greatly elevated intraocular pressure is reached over a long period of several months or several years.

Here, the phrase "rapidly reduce the intraocular pressure" or "rapidly lower the intraocular pressure" means that the intraocular pressure is reduced or lowered to a normal level, for example, in a range from 10 to 25 mmHg and preferably in a range from 10 to 20 mmHg within, for example, 24 hours, preferably 12 hours, more preferably 6 hours, further preferably 4 hours, and especially preferably 2 hours. More specifically, it is suitable to achieve a reduction in intraocular pressure of −1 to −90 mmHg, preferably −5 to −80 mmHg, more preferably −7 to −70 mmHg, further preferably −10 to −70 mmHg, and most preferably −10 to −60 mmHg, for example, within 6 hours, or it is suitable to achieve a reduction in intraocular pressure of −1 to −90 mmHg, preferably −5 to −80 mmHg, more preferably −7 to −70 mmHg, further preferably −10 to −70 mmHg, and most preferably −10 to −60 mmHg, for example, within 2 hours. Here, regarding the negative values, for example, a negative value of "−10 mmHg" means that the intraocular pressure is reduced by 10 mmHg from that before treatment.

In the present invention, examples of the "disease involving a greatly elevated intraocular pressure" include acute primary angle closure, primary angle closure glaucoma, secondary angle closure glaucoma, and acute intraocular pressure elevation such as that caused by inflammation such as uveitis.

Patients with the above-described disease which has to be prevented and/or treated include humans and non-human animals, and, especially, humans and non-human mammals.

EXAMPLES

Hereinafter, Formulation Examples and results of a pharmacological test are shown; however, these are provided for better understanding of the present invention, and do not limit the scope of the present invention.

Formulation Examples

Representative Formulation Examples of the therapeutic agent of the present invention are shown below. Note that, in the following Formulation Examples, the blended amount of each component is an amount in 100 mL of the pharmaceutical preparation. In addition, the present compound A means isopropyl (6-{[4-(pyrazol-1-yl)benzyl](pyridin-3-ylsulfonyl)aminometh yl}pyridin-2-ylamino)acetate.

Formulation Example 1

| Eye drop (in 100 mL) | |
|---|---|
| the present compound A | 0.002 g |
| boric acid | 0.2 g |
| glycerin | 2.0 g |
| polysorbate 80 | 0.5 g |
| disodium edetate | 0.05 g |
| benzalkonium chloride | 0.005 g |
| dilute hydrochloric acid | quantum sufficit |
| sodium hydroxide | quantum sufficit |
| purified water | quantum sufficit |

Formulation Example 2

| Eye drop (in 100 mL) | |
|---|---|
| the present compound A | 0.002 g |
| sodium dihydrogen phosphate | 0.2 g |
| glycerin | 2.0 g |
| vitamin E TPGS | 0.8 g |
| disodium edetate | 0.05 g |
| benzalkonium chloride | 0.005 g |
| dilute hydrochloric acid | quantum sufficit |
| sodium hydroxide | quantum sufficit |
| purified water | quantum sufficit |

Formulation Example 3

| Eye drop (in 100 mL) | |
|---|---|
| the present compound A | 0.002 g |
| trisodium citrate | 0.2 g |
| glycerin | 2.0 g |
| polyoxyethylene hardened castor oil 60 | 0.3 g |
| disodium edetate | 0.05 g |
| benzalkonium chloride | 0.005 g |
| dilute hydrochloric acid | quantum sufficit |
| sodium hydroxide | quantum sufficit |
| purified water | quantum sufficit |

Note that, it is possible to obtain a desired agent by adjusting the types and/or the blended amounts of the present compound A and/or the additives in any of the above-described Formulation Examples 1 to 3, as appropriate.

[Pharmacological Test]

To investigate the usefulness of the present compound A, an intraocular pressure-lowering effect of the present compound A was tested in experimental animals (ocular hypertensive monkeys). Regarding test solutions, a reference solution not containing the present compound A was used as a control, a solution containing the present compound A was prepared as Example 1 of the invention of the present application, and a latanoprost eye drop was prepared as Comparative Example 1, as shown below.
(Preparation of Test Solutions)
(1) Preparation of Reference Solution To 1.7 g of polyoxyl 35 castor oil, 10 mL of a 0.5% (w/v) disodium edetate/10% (w/v) glycerin solution, 1 mL of a 1% (w/v) benzalkonium chloride solution, 30 mL of purified water, and 50 mL of a 2% (w/v) boric acid/0.2% (w/v) sorbic acid solution were added and dissolved therein. After dissolution was achieved, the pH of the pharmaceutical preparation was adjusted to about 6.5 by adding a suitable amount of a sodium hydroxide solution, and the total volume was adjusted to 100 mL by adding a suitable amount of purified water. Thus, a reference solution serving as a control was prepared.

(2) Preparation of Solution of the Present Compound A (Example 1)

To 2.55 g of polyoxyl 35 castor oil, 0.015 g of the present compound A, 15 mL of a 0.5% (w/v) disodium edetate/10% (w/v) glycerin solution, 1.5 mL of a 1% (w/v) benzalkonium chloride solution, 45 mL of purified water, and 75 mL of a 2% (w/v) boric acid/0.2% (w/v) sorbic acid solution were added and dissolved therein. After dissolution was achieved, the pH of the pharmaceutical preparation was adjusted to about 6.5 by adding a suitable amount of a sodium hydroxide solution, and then the total volume was adjusted to 150 mL by adding a suitable amount of purified water. Thus, a 0.01 w/v% solution of the present compound A was prepared (Example 1).

(3) Latanoprost Eye drop (Comparative Example 1)

A commercially available latanoprost eye drop (Trade Name: Xalatan$^{(registered\ trademark)}$ eye drop 0.005% (w/v), instillation amount: 20 µL) was used.

(Preparation of Experimental Animals)

Laser-induced ocular hypertensive monkeys (*Macaca fascicularis*) (sex: male, three groups each consisting of 11 monkeys were prepared in total) were prepared according to the article of Gaasterland and Kupfer (Gaasterland D and Kupfer C., Invest Ophthalmol., 1974, June; 13(6): 455-7).

(Testing Method)

(1) For local anesthesia, one drop of a 0.4% oxybuprocaine hydrochloride eye drop (Trade Name: Benoxil$^{(registered\ trademark)}$ solution 0.4%) was instilled to an eye of each of the experimental animals.

(2) The intraocular pressure was measured immediately before instillation of one of the test solutions (the above-described control, Example 1, and Comparative Example 1), and employed as the initial intraocular pressure.

(3) To the one eye of each of the experimental animals, 20 µL of one of the test solutions was instilled (the other eye was not treated).

(4) After 2 hours, 4 hours, and 6 hours had passed from the instillation of the test solution, one drop of the 0.4% oxybuprocaine hydrochloride eye drop was instilled for local anesthesia to the eye whose intraocular pressure was to be measured, and then the intraocular pressure was measured. In addition, the intraocular pressure was measured three times, and the average value was shown in the results.

Note that this test on the three groups was carried out as a three-group, three-period complete-crossover test in which three types of the test using the control, Example 1, and Comparative Example 1 were conducted on each of the groups three times in differed periods (in three periods).

(Results and Discussion)

Table 1 shows the average intraocular pressure reduction (relative to the initial intraocular pressure) of each of the treated groups at 2 hours, 4 hours, and 6 hours after the administration.

TABLE 1

| Treated group | Average intraocular pressure reduction (vs initial intraocular pressure) (mmHg) | | |
|---|---|---|---|
| | 2 hours after instillation | 4 hours after instillation | 6 hours after instillation |
| Control group | −0.5 | −1.0 | −1.6 |
| Example 1-treated group | −16.2 | −19.3 | −19.7 |
| Comparative Example 1-treated group | −7.4 | −8.9 | −9.3 |

* In Table 1, the "negative sign (−)" has such a meaning that, for example, in the case of −1.0, the intraocular pressure was reduced by 1.0 from the initial intraocular pressure.

As is apparent from Table 1, the intraocular pressure-lowering activity of the present compound A of Example 1 was larger than that in the latanoprost-treated group of Comparative Example 1, and the present compound A of Example 1 exhibited an excellent intraocular pressure-lowering activity no later than 2 hours after the administration.

From the above-described results, it was found that the present compound A rapidly provided an excellent intraocular pressure-lowering effect after the administration in the test on the ocular hypertensive monkeys.

The invention claimed is:

1. A method for treating a disease involving a greatly elevated intraocular pressure, comprising steps of:
    administering isopropyl (6-{[4-(pyrazol-1-yl)benzyl](pyridin-3-ylsulfonyl)aminomethyl}pyridin-2-ylamino)acetate or a salt thereof to a patients with said disease which has to be treated, and
    reducing an intraocular pressure of the patient in a range from 10 to 60 mmHg within 6 hours after the treatment,
    wherein the disease involving a greatly elevated intraocular pressure is selected from the group consisting of acute primary angle closure, primary angle closure glaucoma, secondary angle closure glaucoma and acute intraocular pressure elevation.

2. The method according to claim 1, wherein any other prophylactic and/or therapeutic agent for glaucoma or ocular hypertension than isopropyl (6-{[4-(pyrazol-1-yl)benzyl](pyridin-3-ylsulfonyl)aminomethyl}pyridin-2-ylamino)acetate or a salt thereof is not administered.

3. The method according to claim 1, wherein the disease involving a greatly elevated intraocular pressure is the acute intraocular pressure elevation which is caused by inflammation.

4. The method according to claim 1, wherein the administration is instillation.

5. The method according to claim 4, wherein eyedrop comprising 0.001 to 0.03% (w/v) of the isopropyl (6-{[4-(pyrazol-1-yl)benzyl](pyridin-3-ylsulfonyl)aminomethyl}pyridin-2-ylamino)acetate or the salt thereof is instilled.

* * * * *